US00PP10653P

United States Patent [19]

Gray

[11] Patent Number: Plant 10,653

[45] Date of Patent: Oct. 20, 1998

[54] MANDEVILLA PLANT NAMED 'TROPICAL DREAMS'

[75] Inventor: John F. Gray, Hawthorne, Fla.

[73] Assignee: Lake Area Nursery, Inc., Hawthorne, Fla.

[21] Appl. No.: 910,471

[22] Filed: Jul. 25, 1997

[51] Int. Cl.[6] ..... A01H 5/00

[52] U.S. Cl. ..... Plt./54.1

[58] Field of Search ..... Plt./54.1

*Primary Examiner*—Howard J. Locker

*Assistant Examiner*—Kent L. Bell

*Attorney, Agent, or Firm*—C. A. Whealy

[57] ABSTRACT

A distinct cultivar of Mandevilla plant named 'Tropical Dreams', characterized by its unique green and yellow variegated young foliage and green and white to ivory variegated mature foliage; large bright yellow flowers; and vigorous growth habit.

2 Drawing Sheets

The present invention relates to a new and distinct cultivar of Mandevilla plant, botanically known as *Mandevilla sp.,* and hereinafter referred to by the cultivar name 'Tropical Dreams'.

The new cultivar is a naturally-occurring variegated foliage mutation of an unidentified yellow-flowered, solid green-leaf *Mandevilla sp.*. In 1995, the new cultivar was discovered by the inventor in a controlled environment in Hawthorne, Fla., within a population of plants of the unidentified yellow-flowered, solid green-leaf Mandevilla.

Asexual reproduction of the new cultivar by terminal cuttings taken at Hawthorne, Fla., has shown that the unique features of this new Mandevilla plant are stable and reproduced true to type in successive generations of asexual reproduction.

The cultivar 'Tropical Dreams' has not been observed under all possible environmental conditions. The phenotype may vary somewhat with variations in environment such as temperature and light intensity, without, however, any variance in genotype.

The following traits have been repeatedly observed and are determined to be the unique characteristics of 'Tropical Dreams'. These characteristics in combination distinguish 'Tropical Dreams' as a new and distinct cultivar:

1. Unique green and yellow variegated young foliage and green and white to ivory variegated mature foliage.
2. Large bright yellow flowers.
3. Vigorous growth habit.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of typical plants of the cultivar 'Tropical Dreams' on a trellis.

The photograph on the second sheet comprises a close-up view of typical foliage and flowers of the cultivar 'Tropical Dreams'.

Flower and foliage colors in the photographs may appear different than the actual colors due to light reflectance.

DETAILED BOTANICAL DESCRIPTION

The following observations and measurements describe plants grown in Hawthorne, Fla., in a double polyethylenecovered greenhouse with day temperatures ranging from 21° to 38° and night temperatures ranging from 16° to 21° C.

In the following description, color references are made to The Royal Horticultural Society Colour Chart except where general terms of ordinary dictionary significance are used.

Botanical classification: *Mandevilla sp.* cultivar 'Tropical Dreams'.

Parentage: Naturally-occurring foliage variegation mutation of an unidentified yellow-flowered, solid green-leaf *Mandevilla sp.*.

Propagation:

*Type cutting.*—Terminal vegetative cuttings.

*Time to initiate and develop roots.*—Summer: About 20 days at temperatures of 27° C. Winter: About 30 days at temperatures of 21° C.

*Rooting habit.*—Vigorous, numerous, fibrous, and well-branched.

Plant description:

*Form.*—Upright herbaceous climbing vine that is suitable for trellises.

*Branching habit.*—One lateral branch usually forms per node. Removal of the terminal apex (pinching) stimulates development of lateral branches.

*Plant spread.*—About 20 cm or the width of one leaf pair.

*Vigor.*—Vigorous.

*Growth rate.*—Rapid. About 6 weeks to produce a finished plant in a 10-cm container, approximately 10 cm in height and 20 cm. in width.

*Lateral stem description.*—Internode length: About 7 cm. Diameter: About 3 mm. Texture: Glabrous. Color: Young: 144A/144B. Mature: 144A, becoming woody and grayish green with development.

*Foliage description.*—Leaves large, single, opposite, generally symmetrical, durable and long-persisting. Size (largest leaves): Length: About 9 cm. Width: About 5 cm. Shape: Oblong. Apex: Rounded to acute. Base: Obtuse. Margin: Entire. Texture: Glabrous, smooth and leathery. Upper surface shiny and lower surface dull. Color: Young leaves: Green at center interspersed with light green areas surrounded by yellow variegation. Variegation pattern irregular. Upper surface: Green: 144A/146B. Light green: Close to 148C. Yellow: Yellowish green to 4C. Lower surface: Green: Close to 146B. Light green: Not apparent. Yellow: Yellowish green to 4C. Fully expanded leaves: Green at center interspersed with light green areas surrounded by white to ivory variegation. Variegation pattern irregular. Upper surface: Green: Close to 146B/147B. Light green: 148C or lighter. White to ivory: White to 158C. Lower surface: Green: Close to 146/147B. Light green: 146C/148C. White to ivory: White to 158C. Petiole: Length: About 1.5 cm. Diameter: About 2 mm. Color: 144A.

Flower description:

*Flower type and habit.*—Large, single, tubular pinwheel-shaped flowers that face outward and/or upright. Calyx five-parted, petals fused at base. Numerous flowers per terminal.

*Natural flowering season.*—Spring through summer.

*Flower longevity.*—Flowers open quickly and usually last about one or two days. Flowers self-cleaning.

*Fragrance.*—None.

*Flower diameter.*—About 6.5 cm.

*Flower length.*—About 4 cm.

*Flower tube length.*—About 2.4 cm.

*Petals.*—Appearance: Smooth, satiny. Lower surface and tube, waxy. Quantity: Five, whorled and fused at base. Length: About 2.5 cm above throat. Width: About 2.5 cm. Aspect: Flat or recurved. Shape: Mostly rounded. Apex: Rounded. Margin: Entire. Color: Upper surface: 5A. Lower surface: 5C, waxy. Tube: Greenish yellow, waxy.

*Peduncle.*—Aspect: Straight. Strength: Flexible, but strong. Length: About 1 cm. Color: 144A.

*Flower bud.*—Shape: Elongated tube. Rate of opening: Rapid. Length: About 4 cm. Diameter: About 1 cm. Color: Greenish yellow.

*Calyx.*—Shape: Star of five sepals fused at base. Length: About 7 mm. Diameter: About 4 mm. Sepal shape: Linear, narrow. Sepal apex: Pointed. Sepal margin: Entire. Sepal texture: Waxy. Color: 144A.

*Reproductive organs.*—Androecium: Stamen number: Five. Anther shape: Arrow. Anther size: About 4 mm by 1 mm. Anther color: Yellowish white. Amount of pollen: Moderate. Pollen color: Light yellow. Gynoecium: Pistil length: About 8 mm. Stigma color: Whitish green.

Disease resistance: The new Mandevilla has not been observed to be resistant or tolerant to pathogens common to Mandevilla.

Seed production: Seed production has not been observed.

It is claimed:

1. A new and distinct cultivar of Mandevilla plant named 'Tropical Dreams', as illustrated and described.

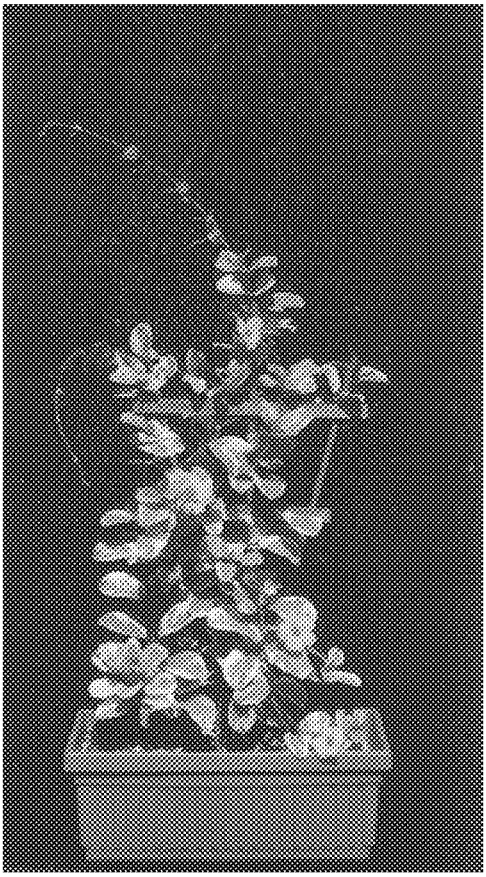

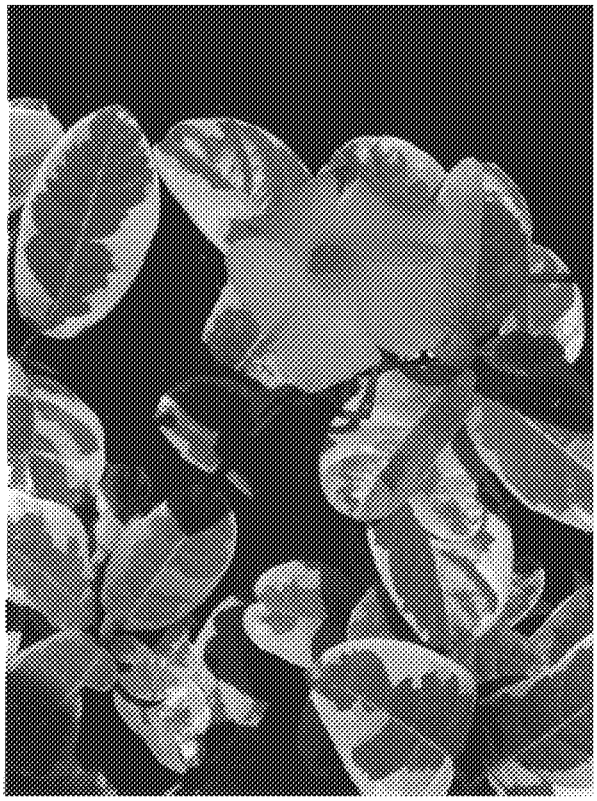

* * * * *